(12) United States Patent
Kotera et al.

(10) Patent No.: US 8,048,840 B2
(45) Date of Patent: Nov. 1, 2011

(54) ETHER COMPOUND

(75) Inventors: Takanori Kotera, Wakayama (JP); Akira Saito, Wakayama (JP)

(73) Assignee: Kao Corporation, Tokyo (JP)

( * ) Notice: Subject to any disclaimer, the term of this patent is extended or adjusted under 35 U.S.C. 154(b) by 29 days.

(21) Appl. No.: 12/664,329

(22) PCT Filed: Jun. 11, 2008

(86) PCT No.: PCT/JP2008/061071
§ 371 (c)(1),
(2), (4) Date: Apr. 16, 2010

(87) PCT Pub. No.: WO2008/153187
PCT Pub. Date: Dec. 18, 2008

(65) Prior Publication Data
US 2010/0197559 A1  Aug. 5, 2010

(30) Foreign Application Priority Data
Jun. 12, 2007  (JP) ................. 2007-154882

(51) Int. Cl.
C07C 41/03  (2006.01)
C07C 43/13  (2006.01)
C11D 1/68  (2006.01)
C11D 3/20  (2006.01)

(52) U.S. Cl. ........ 510/356; 510/505; 510/506; 528/425; 568/300; 568/579; 568/671; 568/675; 568/679; 568/680; 568/700

(58) Field of Classification Search ........... 510/356, 510/505, 506; 528/425; 568/300, 579, 671, 568/675, 679, 680, 700
See application file for complete search history.

(56) References Cited

U.S. PATENT DOCUMENTS
4,576,967 A * 3/1986 Urata et al. ............ 514/772
2002/0035238 A1  3/2002 Nakamura et al.

FOREIGN PATENT DOCUMENTS
| JP | 60-28944 A | 2/1985 |
| JP | 9-188755 A | 7/1997 |
| JP | 2001-49290 A | 2/2001 |
| JP | 2001-114720 A | 4/2001 |
| JP | 2005-89603 A | 4/2005 |

OTHER PUBLICATIONS

Kang et al, "The Synthesis of Oligoglycerol Monolaurates", J. of Korean Ind. & Eng. Chemistry, vol. 4, No. 3, Sep. 1993, pp. 505-514.*
Kleemann, "Glycidol: properties, reactions, applications," Dr. Alfred Hüthig Verlag, Heidelberg, 1981, pp. 58-65, 1981.

* cited by examiner

*Primary Examiner* — Brian P Mruk
(74) *Attorney, Agent, or Firm* — Birch, Stewart, Kolasch & Birch, LLP

(57) ABSTRACT

The present invention provides a novel ether compound represented by formula (1):

$$R-O-CH_2-CH(OH)-CH_2-O-CH(CH_2-O-CH_2-CH(OH)-CH_2-OH)-CH_2-O-CH_2-CH(OH)-CH_2-OH \quad (1)$$

wherein R represents a hydrocarbon group having 4 to 22 carbon atoms.

9 Claims, 4 Drawing Sheets

ETHER COMPOUND

FIELD OF THE INVENTION

The present invention relates to a novel polyglyceryl monoether compound, a surfactant containing the same, a detergent composition containing the same, a polyglyceryl ether composition containing the same, and a method for producing the same.

BACKGROUND OF THE INVENTION

Polyglyceryl ether derivatives are compounds useful for a solvent, an emulsifier, a dispersant, a detergent, a foam-boosting agent, and the like. For producing polyglyceryl ether derivatives, there is a known method of reacting an alcohol with glycidol. Such a method has been conventionally conducted by treating an alcohol with an alkali in general and adding glycidol dropwise thereto to react. There are also known methods, including a method of conducting addition polymerization of an aliphatic alcohol with a glycidyl ester and subjecting the resultant polymer to saponification with an alkali to remove an acyl group (see, JP-A 9-188755), a method of repeating a cycle of reactions to achieve an intended polymerization degree, that cycle includes reacting an alkyl glycidyl ether with glycerol to produce an alkyl diglyceryl ether, condensing a hydroxy group of the ether with an allyl halide, and converting an allyl group to two hydroxy groups (see, JP-A 2001-114720), and a method of conducting addition polymerization of an aliphatic alcohol with glycidol in the presence of a catalyst (see, GLYCIDOL: properties, reactions, applications Kleemann, Axel Dr. Alfred Huthig Verlag Heidelberg 1981).

JP-A 2001-49290 discloses a detergent composition containing a monoalkyl ether of glycerol or polyglycerol prepared from glycerol.

SUMMARY OF THE INVENTION

The present invention relates to a novel ether compound represented by formula (1):

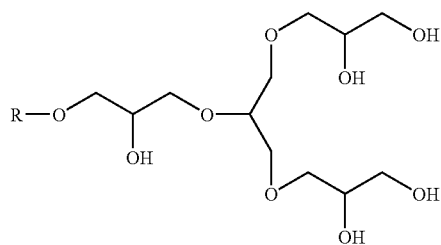

(1)

wherein R represents a hydrocarbon group having 4 to 22 carbon atoms.

The present invention also relates to a method for producing the novel ether compound according to the invention, including reacting a compound represented by formula (2) with an alkyl glycidyl ether:

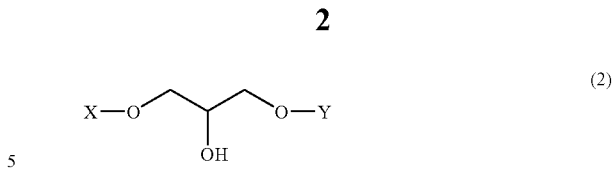

(2)

wherein X and Y each represents a group having a protected group.

The present invention also relates to a surfactant containing the novel ether compound according to the invention.

The present invention also relates to a detergent composition containing the novel ether compound according to the invention.

The present invention also relates to a polyglyceryl ether composition containing (a1) the novel ether compound of the present invention and (a2) a polyglyceryl monoether having a glycerol condensation degree of 1 to 7 and being other than the ether compound (a1), and a detergent composition containing the polyglyceryl ether composition.

The present invention also relates to use of the novel ether compound of the present invention as a surfactant or a detergent.

DETAILED DESCRIPTION OF THE INVENTION

As described above, these conventional glyceryl and polyglyceryl monoethers are required to be further improved to increase detergency when used in a detergent composition.

The present invention provides a novel polyglyceryl monoether having good detergency when used in a detergent, and the like.

The ether compound represented by formula (1) of the present invention exhibits its surface activity efficiently in water and is useful as a surfactant and further as an ingredient used in a detergent composition. The method of the present invention can produce such a novel ether compound efficiently.

The ether compound represented by formula (1) is a polyglyceryl monoether having a skeleton structure in which glycerol skeleton units are regularly-branched in a radial fashion, what is called a dendrimer type polyglycerol.

In formula (1), R represents a hydrocarbon group having 4 to 22 carbon atoms that may include a double bond and/or a branched chain. Examples of the group for R of formula (1) include alkyl and alkenyl groups. The alkyl group having 4 to 22 carbon atoms includes linear and branched alkyl groups. Specific examples of the linear alkyl group include butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, and docosyl group.

Examples of the branched alkyl group include those derived from β-branched alcohols having 9 to 21 carbon atoms prepared by an oxo method of α-olefins having 8 to 20 carbon atoms with carbon monoxide or from α-branched fatty acids and those derived from Guerbet type alcohols prepared by aldol condensation of linear aldehyde compounds having 4 to 10 carbon atoms.

Examples of the linear alkenyl group include palmitoyl, oleyl, linoleyl, and linolenyl group.

For applications such as a detergent for clothing, R is preferably an alkyl group having 10 to 16 carbon atoms, and more preferably 12 to 14 carbon atoms.

The ether compound of the present invention can be produced by reacting the compound represented by formula (2) with an alkyl glycidyl ether:

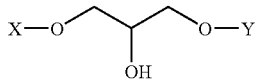

(2)

wherein X and Y each represents a group having a protected group.

In the compound represented by formula (2), each of X and Y is a group having a protected group (protected moiety) against reaction with the alkyl glycidyl ether and providing a glycerol skeleton by deprotection reaction. Each of X and Y may include a carbonyl group and/or an oxy group, and may have a cyclic structure. At least one and preferably both of X and Y have an acetal structure.

In the compound represented by formula (2), at least one of X and Y is preferably, more preferably both are, a group having a protected group and represented by formula (3):

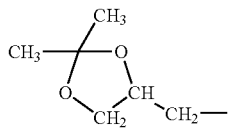

(3)

The compound represented by formula (2) having the group represented by formula (3) can be provided by reaction of glycerol acetal with epihalohydrin or by protection of triglycerol with ketone or aldehyde.

Examples of the group having an acetal structure as represented by formula (3) include the following groups. In these groups, Ph represents a phenyl group.

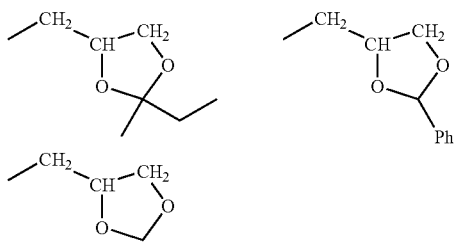

Other examples of the group for X and Y in formula (2) include the following groups. Among these groups, a group represented by formula (3a) which includes silyl group is preferred.

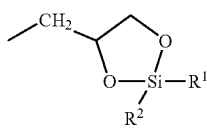

(3a)

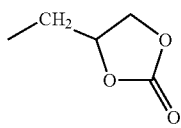

(3b)

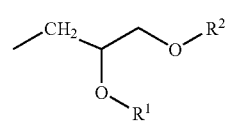

(3c)

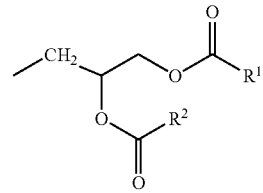

(3d)

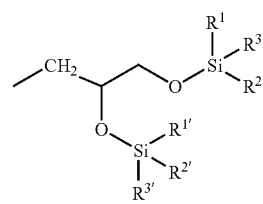

(3e)

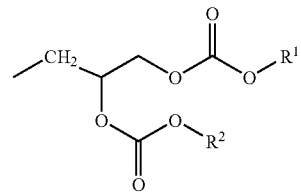

(3f)

wherein $R^1$, $R^2$, $R^3$, $R^{1'}$, $R^{2'}$, and $R^{3'}$ each represents a hydrocarbon group such as methyl, ethyl, isopropyl, allyl, t-butyl, and benzyl group, or an alkyl group such as an alkoxy-substituted methyl group such as methoxymethyl, ethoxymethyl, and benzyloxymethyl group, and may be the same or different.

The alkyl glycidyl ether has preferably an alkyl group of 6 to 20 carbon atoms, and can be prepared from a corresponding alcohol and epihalohydrin. Examples of a commercial product include Epogosey EX, being available from Yokkaichi Chemical Company Limited., cetyl glycidyl ether and stearyl glycidyl ether.

When reacting the compound represented by formula (2) in which both X and Y are groups each represented by formula (3) (compound represented by formula (4)) with the alkyl glycidyl ether (compound represented by formula (5), wherein R preferably represents an alkyl group having 6 to 20 carbon atoms), the ether compound of the present invention can be produced by the following reactions. When a compound represented by formula (2) in which both X and Y are other groups is used, the reactions are essentially similarly performed.

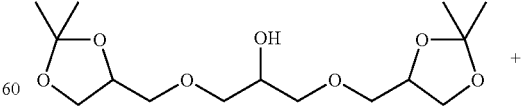

(4)

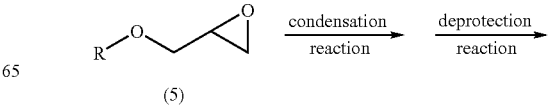

(5)

-continued

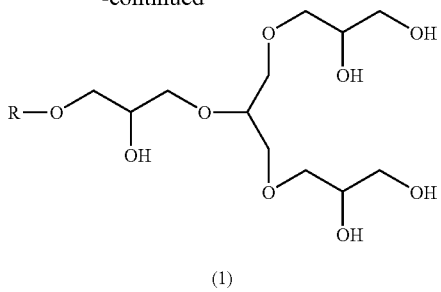

(1)

In the reaction of the compound represented by formula (2), particularly the compound represented by formula (4) with an alkyl glycidyl ether, a molar ratio of both compounds is 0.01 to 10 mol, preferably 0.1 to 5 mol, more preferably 0.1 to 3 mol, and even more preferably 0.1 to 1.5 mol of the alkyl glycidyl ether to 1 mol of the compound represented by formula (2), particularly the compound represented by formula (4).

The reaction may be performed in the absence of a catalyst, or in the presence of an acid catalyst or an alkali catalyst. A catalyst used in the reaction is not specifically limited. Examples of the catalyst include acid catalysts such as $BF_3.OEt_2$, $TiCl_4$, $SnCl_4$, $AlCl_3$, sulfuric acid, perchloric acid, p-toluenesulfonic acid, trifluoromethanesulfonic acid, and trifluoroacetic acid, and alkali catalysts such as metal hydroxides (e.g., LiOH, NaOH, KOH, $Mg(OH)_2$), metal hydrides (e.g., LiH, NaH, KH), metal alcoholates represented by formula $(R^1O)_mM^1$ ($R^1$ represents an alkyl group, $M^1$ represents a metal element, and m represents an ionic valency of the metal), and organometal reagents (e.g., n-butyllithium, t-butyllithium, naphthalene potassium, Grignard reagents). Among these catalysts, $BF_3.OEt_2$, $TiCl_4$, p-toluenesulfonic acid, metal hydroxides, and metal hydroxides have high activity and are preferred. Particularly preferred are NaOH, KOH, sodium hydride, potassium hydride, sodium methoxide, potassium methoxide, sodium t-butoxide, and potassium t-butoxide, because these have usefulness and high activity.

An amount of the catalyst used can be adequately selected according to an activity of the catalyst, an amount and a concentration of the alkyl glycidyl ether used, and the like. The amount is preferably 0.001 to 2 molar equivalents, more preferably 0.005 to 1.5 molar equivalents, and even more preferably 0.01 to 1.0 molar equivalents to the compound of formula (2).

The reaction may be performed without solvent or optionally with an organic solvent in order to assist in mixing raw materials. Examples of the organic solvent include hexane, diethyl ether, tetrahydrofuran, dichloromethane, acetonitrile, nitromethane, benzene, toluene, xylene, chloroform, cyclohexane, dimethylsulfoxide, dimethylformamide, and dimethylacetamide. The reaction may be performed in the air, but preferably in an inert gas, for example, under the atmosphere of nitrogen or argon, in order to prevent generation of bi-products.

A reaction temperature is varied depending on the type of alkyl glycidyl ether used, the type of catalyst used, and an amount thereof. Considering a practical reaction time, an yield, and the like, the reaction temperature is generally 0 to 200° C., preferably 30 to 170° C., and more preferably 50 to 150° C. A reaction time is adequately determined considering reaction conditions and the like. The time is generally 30 minutes to 100 hours, preferably 1 to 50 hours, and more preferably 1 to 30 hours. From the viewpoint of preventing a side-reaction and the like, the alkyl glycidyl ether is preferably introduced into the reaction system by dropping.

After the end of the reaction, a reaction liquid is washed as need, and treated by filtration, distillation, extraction, and the like, and can be purified by standard methods such as silica gel column chromatography, distillation, and recrystallization as need.

The product of the condensation reaction in the scheme can be subjected to deprotection to give the novel ether compound of the present invention. In the reaction of the compound represented by formula (2) in which both X and Y are groups each represented by formula (3) (compound represented by formula (4)) with the alkyl glycidyl ether (compound represented by formula (5), wherein R preferably represents an alkyl group having 6 to 20 carbon atoms), the deprotection can be performed through known reactions such as hydrolysis and solvolysis. After the end of the deprotection reaction, a reaction liquid can be washed as need, and then treated by filtration, desalination, distillation, extraction, and the like to give an intended novel ether compound. The resultant compound can be further purified by standard methods such as silica gel column chromatography, distillation, and recrystallization as need.

The novel ether compound of the present invention can be used as a surfactant, particularly a nonionic surfactant by itself, or diluted in water to give a surfactant composition. The surfactant can be used in any application in any form without specific limitation. For example, the surfactant may be in a form of absolute compound, aqueous solution, aqueous dispersion, emulsion containing other oil phase, water-containing gel, alcohol solution, alcohol dispersion, or in a state of mixed, immersed, or impregnated with a solid substance such as oil gel and wax.

The novel ether compound of the present invention can be widely used in applications such as foods, cosmetics, perfumes, detergents, pesticides, and medicines, as an emulsifier, solubilizer, dispersant, detergent, foaming agent, defoaming agent, penetrant, or antibacterial agent, for emulsifying, solubilizing, dispersing, washing, foaming, defoaming, penetrating, or controlling bacteria, in the form described above. The novel ether compound is particularly good for a detergent.

The ether compound of the present invention is a polyglyceryl ether and can be used together with other polyglyceryl ether to give a polyglyceryl ether composition. Examples of the composition include a polyglyceryl ether composition (hereinafter, referred to as component (a)) containing (a1) the novel ether compound of the present invention (hereinafter, referred to as component (a1)) and (a2) a polyglyceryl monoether having a glycerol condensation degree of 1 to 7 other than the ether compound (a1) (hereinafter, referred to as component (a2)) In applications for detergent composition, a percentage of component (a1) in the component (a) is preferably 0.1% by mass or more, more preferably 3 to 100% by mass, even more preferably 5 to 100% by mass, even more preferably 10 to 100% by mass, even more preferably 20 to 100% by mass, and even more preferably 50 to 100% by mass. In the range, good detergency at low temperature can be achieved.

According to the present invention, a detergent composition containing the ether compound of the present invention and a detergent composition containing the component (a) are provided. An example of the detergent composition includes that containing the component (a) and (b) an alkali agent (hereinafter, referred to as component (b)).

Examples of the component (b) include carbonates, bicarbonates, silicates, orthosilicates, metasilicates, crystalline silicates, and phosphates. Salts are preferably alkaline metal salts such as sodium and potassium salts. These alkali agents may be used alone or as a mixture thereof. Specific examples of the alkali agent include sodium carbonate, potassium carbonate, sodium hydrogen carbonate, sodium silicate No. 1, sodium silicate No. 2, sodium silicate No. 3, sodium tetraborate, sodium pyrophosphate, and sodium tripolyphosphate. As used herein, the crystalline silicate refers an alkali substance that produces 0.1% by mass dispersant having the maximum pH of 11 or more in ion-exchanged water at 20° C. and requires 5 ml or more of 0.1N—HCl aqueous solution to reduce the pH of 1 L of the dispersant to 10. The crystalline silicate is distinguished from a zeolite (crystalline aluminosilicate). The crystalline silicate is preferably in a lamellar form. Those can be used, described in JP-A 7-89712, JP-A 60-227895, and Phys. Chem. Glasses. 7, p 127-p 138 (1966), and Z. Kristallogr., 129, p 396-p 404 (1969), for example. A crystalline silicate represented by formula: $0.42Na_2O.0.14K_2O.SiO_2.0.03CaO.0.005MgO$ is preferably used. Powder and granules of crystalline silicate are also commercially available from Hoechst, which are called "Na-SKS-6" ($\delta$-$Na_2Si_2O_5$).

The detergent composition of the present invention, particularly that for clothing, can further contain a surfactant, a zeolite, and other components known in the art of detergent for clothing in addition to the components (a) and (b).

The detergent composition of the present invention, particularly that for clothing, can further contain a surfactant other than the component (a). Examples of the surfactant other than the component (a) include one of an anionic, nonionic, amphoteric or cationic surfactant or a mixture thereof. Preferred are anionic and nonionic surfactants.

Examples of the anionic surfactant include sulfates of alcohols having 10 to 18 carbon atoms, sulfates of alcohol alkoxylates having 8 to 20 carbon atoms, alkylbenzenesulfonates, alkylsulfates, paraffin sulfonates, $\alpha$-olefin sulfonates, $\alpha$-sulfofatty acid salts, $\alpha$-sulfofatty acid alkyl ester salts, and fatty acid salts. In the present invention, preferred are alkylbenzenesulfonates having a linear alkyl chain of 10 to 14 carbon atoms, and more preferably 12 to 14 carbon atoms. Preferred counter ions thereof are alkaline metals and amines. Particularly preferred are sodium and/or potassium, monoethanolamine, and diethanolamine.

Preferred examples of the nonionic surfactant include polyoxyalkylene alkyl (8 to 20 carbon atoms) ethers, alkyl polyglycosides, polyoxyalkylene alkyl (8 to 20 carbon atoms) phenyl ethers, polyoxyalkylene sorbitan fatty acid (8 to 22 carbon atoms) esters, polyoxyalkylene glycol fatty acid (8 to 22 carbon atoms) esters, and polyoxyethylene/polyoxypropylene block polymers. Particularly preferred for the nonionic surfactant are polyoxyalkylene alkyl ethers produced by adding 4 to 20 mol of alkylene oxide such as ethylene oxide and propylene oxide to an alcohol having 10 to 18 carbon atoms [e.g., those having an HLB value of 10.5 to 15.0, and preferably 11.0 to 14.5 (calculated by the Griffin's method)].

The silicate compound used in the present invention can be selected from those widely used as a builder for detergent. Examples thereof include crystalline or amorphous aluminosilicates and silicates. Particularly preferred is a zeolite.

The zeolite is preferably a compound represented by formula (c1), and more preferably a compound represented by formula (c2):

$$a(M_2O).Al_2O_3.b(SiO_2).w(H_2O) \quad (c1)$$

wherein M represents an alkaline metal atom; a, b, and w represent molar ratios of ingredients, respectively, generally satisfying $0.7 \leq a \leq 1.5$, $0.8 \leq b \leq 6$, and w being an arbitrary positive number, $$Na_2O.Al_2O_3.n(SiO_2).m(H_2O) \quad (c2)$$

wherein n represents the number of 1.8 to 3; and m represents the number of 1 to 6.

Examples of the zeolite include synthetic zeolites such as A, X, and P zeolites. A preferred average particle diameter of the zeolite is 0.1 to 10 μm.

The detergent composition of the present invention, particularly that for clothing, can further contain an organic builder and/or an inorganic builder other than the component (b) and the zeolite. Examples of the organic builder include carboxylates such as aminocarboxylates, hydroxyaminocarboxylates, hydroxycarboxylates, cyclocarboxylates, maleic acid derivatives and oxalates, and organocarboxylic acid (salt) polymers such as polymer or copolymer of acrylic acid, polymer or copolymer of polycarboxylic acid, glyoxylic acid polymers, polysaccharides and salts thereof. Organocarboxylic acid (salt) polymers are particularly preferred. For salts of these builders, a counter ion is preferably an alkaline metal salt or an amine, and particularly preferably a sodium and/or potassium, monoethanolamine, or diethanolamine. These builders may be used alone or in combination.

The detergent composition of the present invention, particularly that for clothing, can further contain additives such as a bleach (e.g., a percarbonate, a perborate, a bleaching activator), an anti-restaining agent (e.g., carboxymethylcellulose), a softener (e.g., a dialkyl type quaternary ammonium salt, clay mineral), a reducing agent (e.g., a sulfite), a fluorescent brightening agent (e.g., a biphenyl type, an aminostilbene type), a foam-controlling agent (e.g., silicone), a fragrance, and an enzyme (e.g., protease, cellulase, pectinase, amylase, lipase).

When the composition is in the form of granule, from the viewpoints of fluidity and anti-caking properties, it may be subjected to surface modification. For a surface modifier, zeolite can be used. Examples of other surface modifiers include silicate compounds such as calcium silicate, silicon dioxide, bentonite, talc, clay or amorphous silica derivatives, metal soap, fine powders such as powdery surfactant, water-soluble polymers such as carboxymethylcellulose, polyethylene glycol, polycarboxylates such as sodium polyacrylate or copolymers of acrylic acid and maleic acid or salts thereof, and fatty acids. Preferably used is the zeolite. Among those used as the component (b), crystalline silicate is preferably used because it also has effects of surface modification.

The detergent composition of the present invention, particularly that for clothing, preferably contains the component (a1) in an amount of 0.1 to 80% by mass, more preferably 1 to 40% by mass, and even more preferably 3 to 20% by mass.

The detergent composition of the present invention, particularly that for clothing, also can contain the component (a) in an amount of 0.1 to 80% by mass, more preferably 1 to 40% by mass, and even more preferably 3 to 20% by mass.

The detergent composition for clothing of the present invention can further contain (a') a polyglyceryl alkyl ether [hereinafter, referred to as component (a')] other than components (a1) and (a2).

The detergent composition of the present invention, particularly that for clothing, preferably contains the component (b) in an amount of 1 to 90% by mass, more preferably 5 to 50% by mass, and even more preferably 10 to 40% by mass.

The detergent composition of the present invention, particularly that for clothing, preferably contains a surfactant other than the component (a) in an amount of 0.1 to 50% by mass, more preferably 3 to 30% by mass, and even more preferably 5 to 15% by mass.

The detergent composition of the present invention, particularly that for clothing, preferably contains the zeolite in an amount of 1 to 90% by mass, more preferably 5 to 50% by mass, and even more preferably 10 to 40% by mass.

The detergent composition of the present invention, particularly that for clothing, preferably contains an inorganic salt other than the component (b) in an amount of 0.1 to 80% by mass, more preferably 5 to 50% by mass, and even more preferably 10 to 40% by mass.

The detergent composition of the present invention, particularly that for clothing, may be in the form of liquid or powder. When it is in the form of powder, from the point of detergency, it preferably has a bulk density of 300 to 1000 g/L, more preferably 500 to 900 g/L, and even more preferably 600 to 800 g/L. It also preferably has an average particle diameter of 150 to 3000 μm, more preferably 500 to 1500 μm, and even more preferably 600 to 1200 μm.

When it is in the form of liquid, from the point of solubility, it preferably has a viscosity of 1 to 1000 mmPa·s, more preferably 10 to 500, and even more preferably 50 to 300. It also preferably has a pH of 4 to 13, more preferably 5 to 11, and even more preferably 7 to 11.

EXAMPLES

The following Examples demonstrate the present invention. Examples are intended to illustrate the present invention and not to limit the present invention.

Example 1

A novel ether compound of (III) was prepared according to the scheme below.

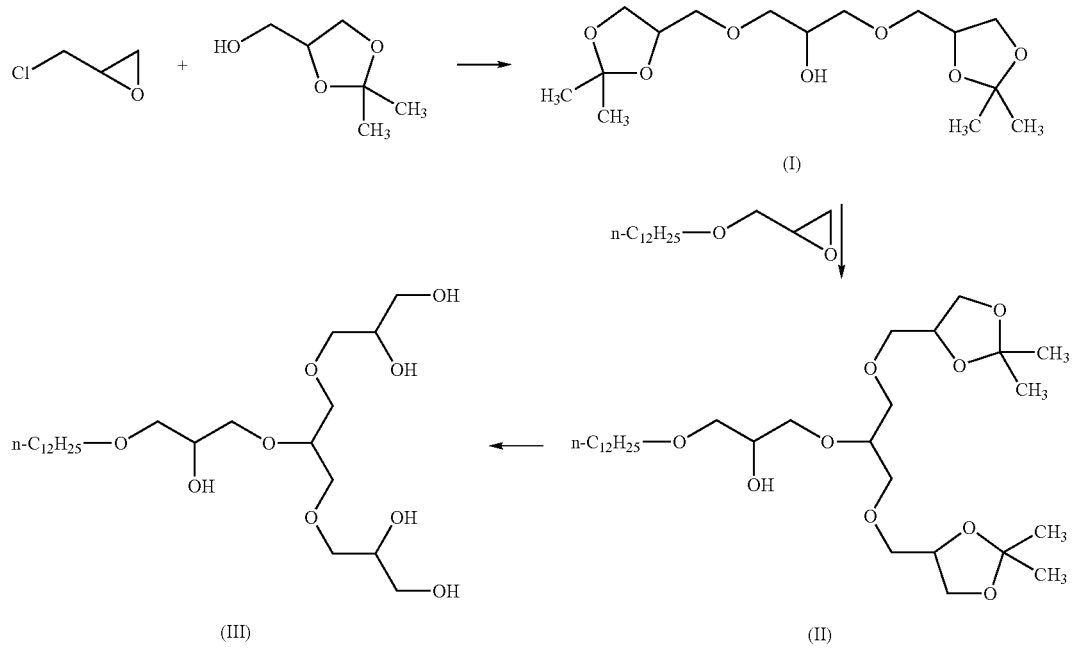

To a 3 L four-neck flask equipped with a stirrer, a nitrogen introducing pipe, and a temperature indicator, 333 g of epichlorohydrin and 1500 g of 2,2-dimethyl-1,3-dioxolan-4-methanol were added, stirred and warmed to 40° C. To this was added 450 g of 48% aqueous solution of sodium hydroxide dropwise for 90 minutes. A mixture was heated and stirred for 20 hours. After the reaction ended, to the mixture was added 1000 g of water and allowed to stand. Separated organic layer was collected. The collected organic layer was purified by distillation at 190° C. under 0.2 kPa to give 755 g of compound (I).

Figure 1:
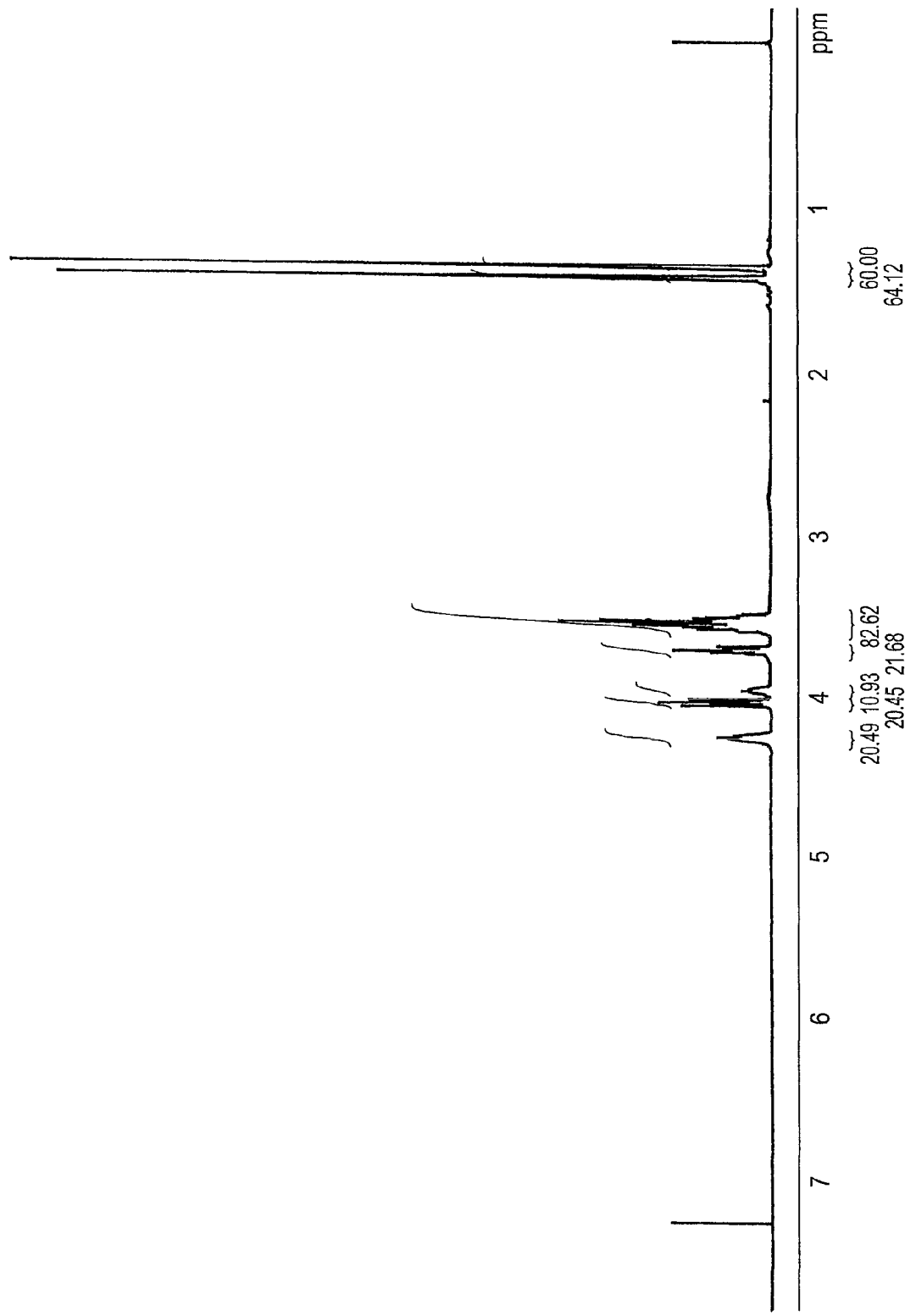
FIG. 1 shows a chart of $^1$H-NMR spectroscopy of the compound (I) prepared in Example.

The result of nuclear magnetic resonance spectroscopy of the compound (I) is shown in FIG. 1 ($^1$H, deuterated chloroform solvent). A part of the compound (I) was subjected to trimethylsilylation of hydroxy group with TMS-I available from GL Sciences Inc. and analyzed with a gas chromatography mass spectroscopy apparatus. The results showed that it was a single compound having a molecular weight of 393 and a formula of $C_{18}H_{36}O_7Si$, which were in agreement with the theoretical values. From these results, it was confirmed that the compound (I) had a structure as shown in the scheme.

To a 200 ml four-neck flask equipped with a stirrer, a nitrogen introducing pipe, and a temperature indicator, 16.0 g of the compound (I) and 0.1 g of sodium hydride were added, stirred and heated to 120° C. To this was added 6.05 g of lauryl glycidyl ether dropwise for 90 minutes. A mixture was heated and stirred for three hours. After being cooled to a room temperature, to the mixture was added water and extracted with ethyl acetate to separate organic matters. The organic solvent was evaporated, and the residue was purified by silica gel column chromatography to give 4.5 g of compound (II).

To a 500 ml four-neck flask equipped with a stirrer, a Dean-Stark apparatus, a condenser, and a temperature indicator, 4.5 g of the compound (II), 200 g of ethanol, 20 g of water, and 2 g of 0.1M sulfuric acid were added, stirred and heated to 95° C. to continuously remove solvents and acetone. After the reaction ended, to the residue were added water and 4 g of 0.1M aqueous solution of sodium hydroxide. A mixture was passed through cation exchange resin and anion exchange resin to desalt, and dehydrated under reduced pressure to give 3.8 g of compound (III).

Figure 2:
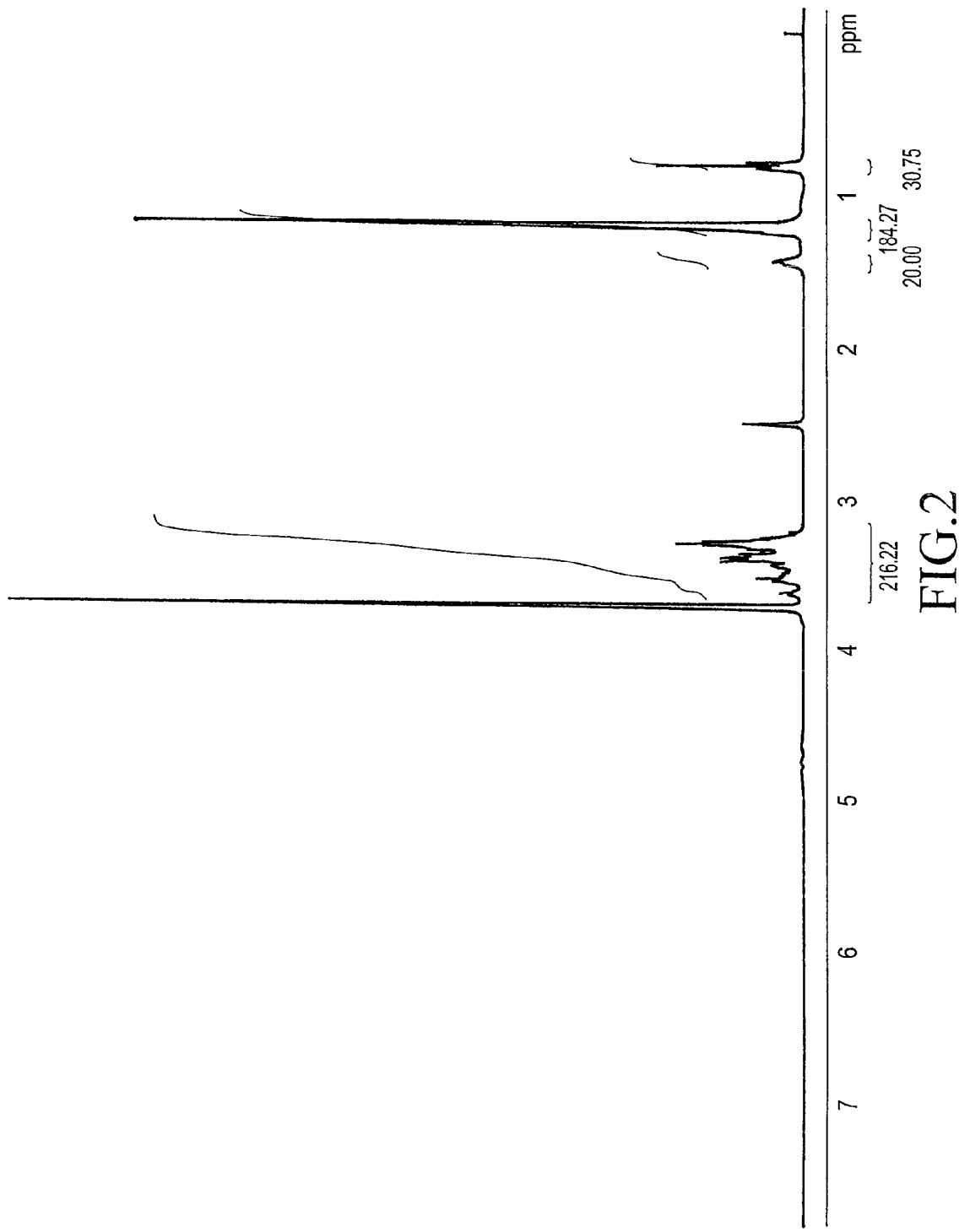
FIG. 2 shows a chart of $^1$H-NMR spectroscopy of the compound (III) prepared in Example.
Figure 3:
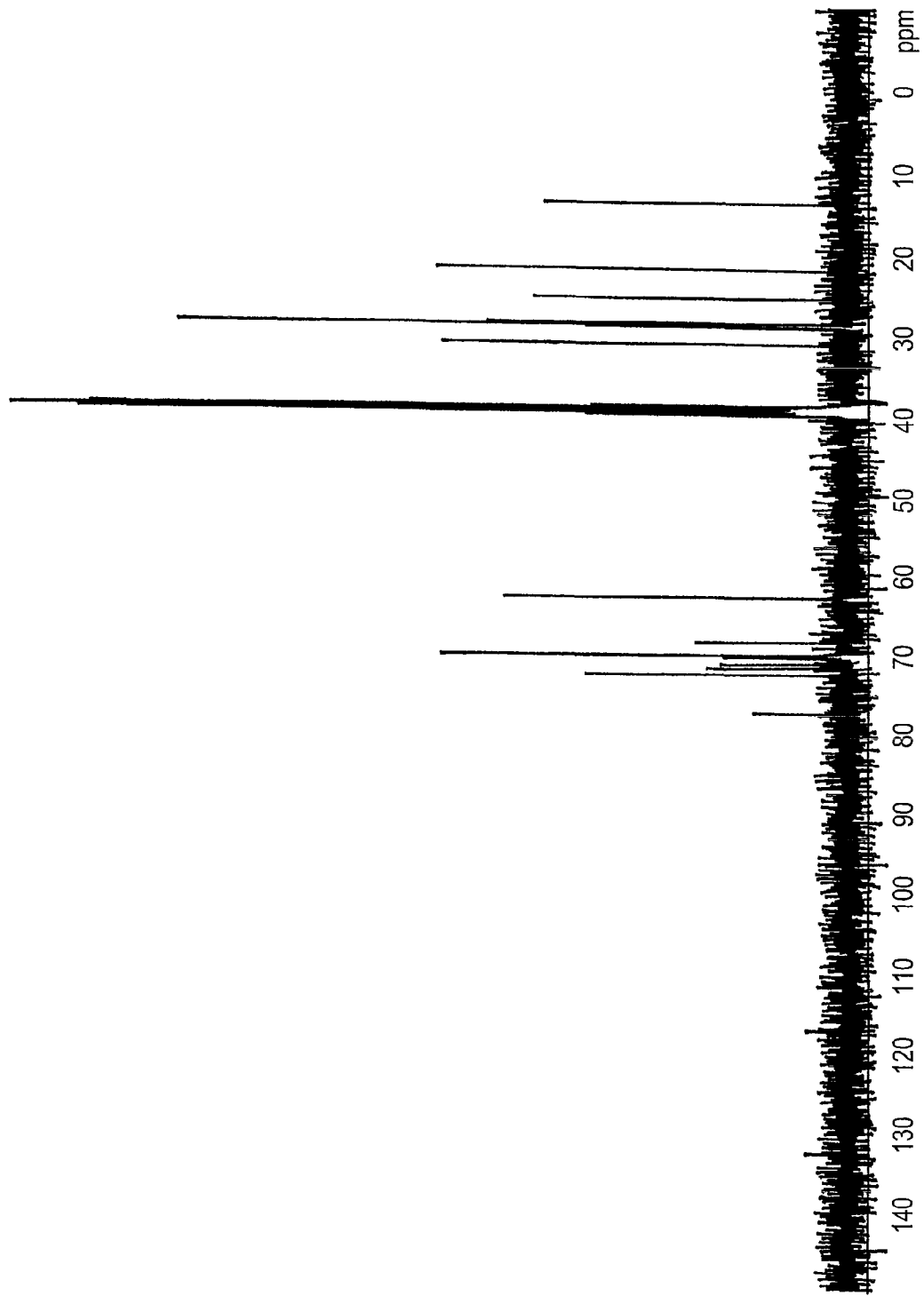
FIG. 3 shows a chart of $^{13}$C-NMR spectroscopy of the compound (III) prepared in Example.

The compound (III) was subjected to nuclear magnetic resonance spectroscopy and infrared absorption spectroscopy. FIG. 2 shows a $^1$H-NMR spectrum data in deuterated dimethylsulfoxide containing deuterium oxide, FIG. 3 shows a $^{13}$C-NMR spectrum data, and FIG. 4 shows an infrared absorption spectrum (liquid film).

Figure 4:
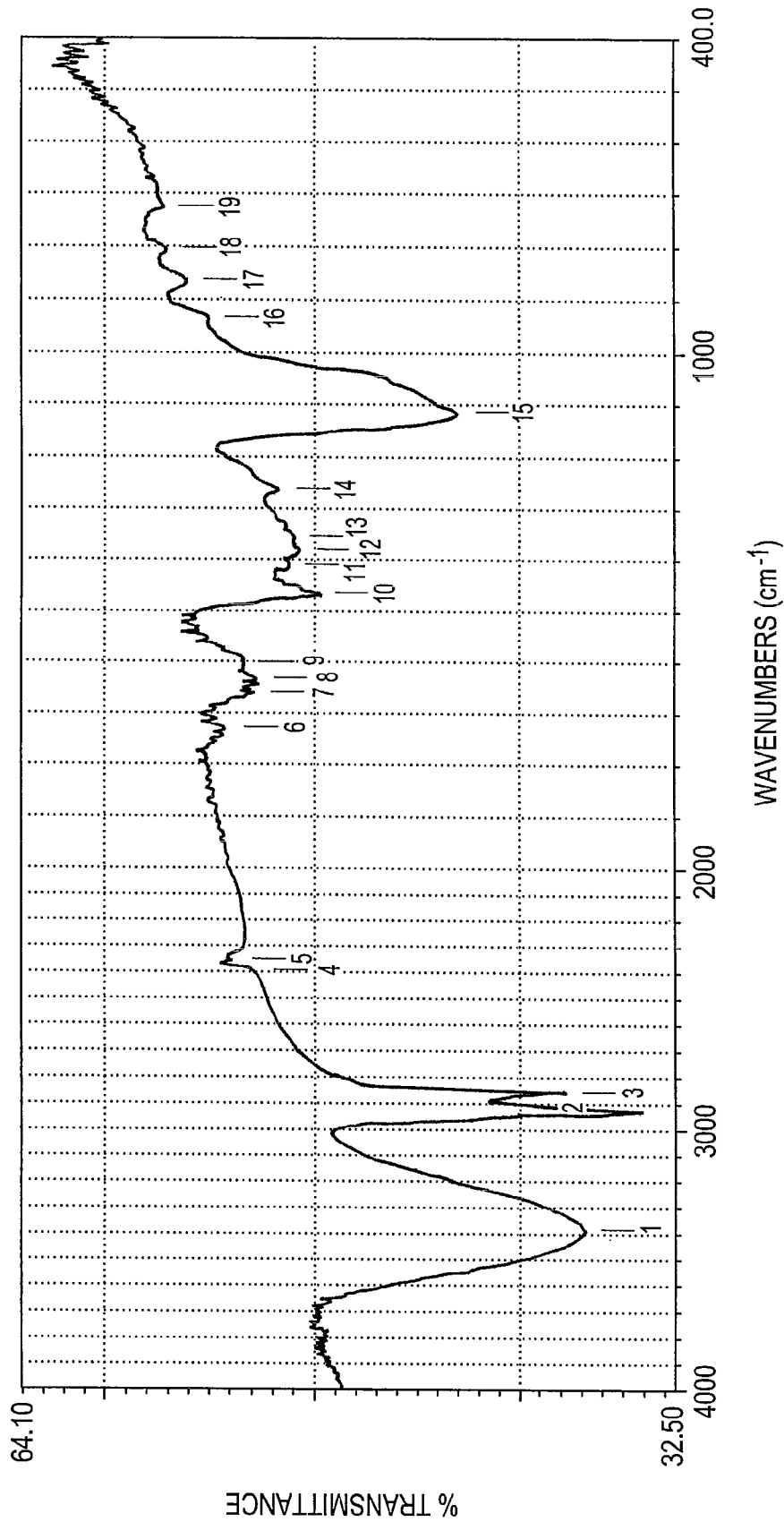
FIG. 4 shows a chart of Infrared absorption spectroscopy of the compound (III) prepared in Example.

The data of the infrared absorption spectrum in FIG. 4 are as follows. Wave numbers (cm$^{-1}$) and transmittance(%) of numbered peaks are shown.

| Peak number | wave number (cm-1) | transmittance (%) |
|---|---|---|
| 01 | 3384.46 | 36.8249 |
| 02 | 2923.56 | 34.0559 |
| 03 | 2854.13 | 37.7255 |
| 04 | 2391.30 | 52.8295 |
| 05 | 2348.87 | 53.8428 |
| 06 | 1725.98 | 54.2076 |
| 07 | 1658.48 | 52.9277 |
| 08 | 1631.48 | 52.8381 |
| 09 | 1598.70 | 53.4037 |
| 10 | 1461.78 | 49.7927 |
| 11 | 1407.78 | 51.2103 |
| 12 | 1378.85 | 50.6779 |
| 13 | 1351.86 | 50.9575 |
| 14 | 1261.22 | 51.6533 |
| 15 | 1114.65 | 42.9477 |
| 16 | 931.449 | 55.0448 |
| 17 | 860.096 | 56.1103 |
| 18 | 802.242 | 57.1054 |
| 19 | 723.175 | 57.2332 |

0.05 g of the compound (III) was mixed with TMS-I available from GL Sciences Inc. and heated and stirred to trimethylsilylate a hydroxy group. The product was analyzed with a gas chromatography mass spectroscopy apparatus. The result showed a single peak corresponding to a molecular weight of 843 and a formula of $C_{39}H_{90}O_9Si_5$, which were in agreement with the theoretical values. From these spectrum data, it was confirmed that the compound (III) had a structure as shown in the scheme (R in formula (1) is a linear alkyl group having 12 carbon atoms)

Analysis apparatus and measurement conditions used in Example 1 are as follows.

<Nuclear Magnetic Resonance Apparatus>

Marcury-400BB, Varian, Inc.

Measurement Conditions $^1$H NMR . . . 400 MHz, relaxation time: 1 second, accumulation: 8 times, room temperature $^{13}$C NMR . . . 100 MHz, relaxation time: 1 second, accumulation: 512 times, room temperature Detailed measurement conditions of the $^1$H-NMR spectrum data of the compound (I) (FIG. 1), the $^1$H-NMR spectrum data of the compound (III) (FIG. 2), and the $^{13}$C-NMR spectrum data of the compound (III) (FIG. 3) are as follows, respectively.

Archive directory: /export/home/vnmr1/vnmrsys/data
Sample directory: sk31_saito_TGly-ketal_06Jun2007
Pulse Sequence s2pul
Solvent CDCl3
Ambient temperature
Sample #51
File: PROTON
Mercury-400BB "wsintol-1-011"
PULSE SEQUENCE
Relax. delay 10.000 sec
Pulse 45.0 degrees
Acq. time 3.280 sec
Width 6410.3 Hz
8 repetitions
OBSERVE H1, 400.4242225 MHz
DATA PROCESSING
FT size 65536
Total time 2 min, 5 sec
Archive directory: /export/home/vnmr1/vnmrsys/data
Sample directory: sk31_saito_TeGE20D_w-D20_06Jun2007
Pulse Sequence: s2pul
Solvent: DMSO
Ambient temperature
Sample #51
File: PROTON
Mercury-400BB "wsintol-011"
PULSE SEQUENCE
Relax. delay 10.000 sec
Pulse 45.0 degrees
Acq. time 3.280 sec
Width 6410.3 Hz
8 repetitions
OBSERVE H1, 400.4261284 MHz
DATA PROCESSING
FT size 65536
Total time 2 min, 5 sec
Archive directory: /export/home/vnmr1/vnmrsys/data
Sample directory: sk31_saito_TeGE20D_06Jun2007-09:05:02
Pulse Sequence: s2pul
Solvent DMSO
Ambient temperature
Sample #51
File: CARBON
Mercury-400BB "wsintol-011"
PULSE SEQUENCE
Relax. delay 1.000 sec
Pulse 45.0 degrees
Acq. time 1.199 sec
Width 25188.9 Hz
512 repetitions
OBSERVE C13, 100.6872502 MHz
DECOUPLE H1, 400.4280764 MHz
Power 39 dB
continuously on
WALTZ-16 modulated
DATA PROCESSING
Line broadening 1.0 Hz
FT size 65536
Total time 19 min, 32 sec
<Infrared Spectroscopy Apparatus>
FT-710, HORIBA, Ltd.

Example 2

Detergent compositions shown in Table 1 were prepared with the following ingredients, and evaluated for detergency by the method described below. Results are shown in Table 1.

a1-1: dendrimer type tetraglycidyl polylauryl ether prepared in Example 1 [component (a1):100% by mass]

a2-1: polyglyceryl lauryl ether prepared by reacting lauryl alcohol with glycidol at a molar ratio of 1:4 in the presence of an alkali catalyst [component (a1): 0% by mass]

LAS: NEOPELEX G-15, Kao Corporation zeolite: 4A zeolite having an average particle diameter of 3 μm, Tosoh Corporation

[1] Method for Evaluating Detergency

To 1 L each of tap water were added 0.6667 g each of detergent compositions shown in Table 1 and dissolved. To these each were added five pieces of cloth stained with meat sauce, which was prepared as described below, and washed for 10 minutes with a Terg-O-Tometer at 80 round/min and 20° C. or 5° C. (each was liquid temperature). Test pieces were sufficiently rinsed and dried. A washing rate was measured according to the following formula.

washing rate (%)=(reflectance after washing-reflectance before washing)/(reflectance of clean cloth-reflectance before washing)*100

A reflectance was measured using NDR-10DP manufactured by Nippon Denshoku Industries Co., Ltd. with a 460 nm filter.

<Preparation of Cloth Stained with Meat Sauce>

Commercially available meat sauce (Kanjuku Tomato no Meat Sauce, manufactured by Kagome Co., Ltd) was heated to 50° C., and passed through a 710 μm-mesh filter to separate solid matters from liquid. 0.4 mL of the obtained liquid was uniformly applied on 6 cm by 6 cm of cotton test cloth #2023, and dried for 15 hours at 20° C. and 65% RH. The dried cloth was used in the test.

parts by mass of aqueous solution of 40% by mass sodium polyacrylate, and stirred for 10 minutes. To this were further added 40 parts by mass of sodium chloride and 160 parts by mass of zeolite, and stirred for 15 minutes to give uniform slurry (water content in slurry: 50% by mass). A final temperature of the prepared slurry was 50° C.

The slurry was supplied to a spray-drying tower (counter flow type) with a pump, and sprayed through a pressure spraying nozzle mounted near the top of the tower at a spray pressure of 2.5 MPa. Hot gas was supplied to the spray drying tower from the bottom at 285° C. and discharged from the top at 98° C. The resultant spray-dried particles 1 had a water content of 0.0%, a bulk density of 510 g/L, and an average particle diameter of 290 μm.

(Preparation of a Surfactant Composition)

400 parts by mass of polyoxyethylene alkyl ether and 69 parts by mass of polyethylene glycol (solid content: 60% by mass) were heated to 80° C. To this were added 3 parts by mass of component a1-1 and 440 parts by mass of component a2-1, which were used in Example 2, 960 parts by mass of dodecylbenzensulfonic acid, and 258 parts by mass of aqueous solution of 48% sodium hydroxide, and stirred to give a surfactant composition.

(Preparation of Detergent Particles)

The prepared surfactant composition were heated to 80° C. Into a Loedige mixer (Matsuzaka Giken Co., Ltd., volume: 130 L, equipped with a jacket), 50 parts by mass of the spray-dried particles prepared above and 9.332 parts by mass of sodium carbonate were charged and stirred with a main shaft (for an agitating blade, rotation number: 60 rpm, circumferential velocity: 1.6 m/s). In stirring, warm water of 80°

TABLE 1

| | | | | Example | | | | | | | | | | Comparative example | | |
|---|---|---|---|---|---|---|---|---|---|---|---|---|---|---|---|---|
| | | | | 2-1 | 2-2 | 2-3 | 2-4 | 2-5 | 2-6 | 2-7 | 2-8 | 2-9 | 2-10 | 2-11 | 2-1 | 2-2 | 2-3 |
| Compounding components (mass %) | (a) | (a1) | a1-1 | 20 | 25 | 35 | 10 | 5 | 3 | 0.5 | 0.1 | 15 | 5 | 0.5 | | | |
| | | (a2) | a2-1 | | | | 10 | 15 | 17 | 19.5 | 19.9 | 20 | 30 | 34.5 | 20 | 25 | 35 |
| | | LAS | | 15 | 10 | | 15 | 15 | 15 | 15 | 15 | | | | | 15 | 10 |
| | (b) | Sodium carbonate | | 20 | 20 | 20 | 20 | 20 | 20 | 20 | 20 | 20 | 20 | 20 | 20 | 20 | 20 |
| | | Sodium sulfate | | 15 | 15 | 15 | 15 | 15 | 15 | 15 | 15 | 15 | 15 | 15 | 15 | 15 | 15 |
| | | zeolite | | 30 | 30 | 30 | 30 | 30 | 30 | 30 | 30 | 30 | 30 | 30 | 30 | 30 | 30 |
| | | Total | | 100 | 100 | 100 | 100 | 100 | 100 | 100 | 100 | 100 | 100 | 100 | 100 | 100 | 100 |
| Detergency (%) | | 20° C. | | 82 | 85 | 92 | 81 | 79 | 80 | 79 | 78 | 90 | 91 | 90 | 78 | 83 | 91 |
| | | 5° C. | | 68 | 71 | 75 | 67 | 63 | 62 | 60 | 60 | 73 | 70 | 62 | 35 | 42 | 50 |

As shown in Table 1, detergent compositions containing the novel ether compound of the present invention had increased detergency at both 20° C. and 5° C. Therefore, it is understood that the novel ether compound of the present invention has good water-solubility. It was confirmed that a mixture of water and oil was emulsified with addition of the compound a1-1.

Example 3

Detergent particles 1 containing the novel ether compound of the present invention were prepared by the following procedure.

(Preparation of Spray-Dried Particles)

Into a mixing tank, 410 parts by mass of water was poured and warmed to 45° C. To this were added 110 parts by mass of sodium sulfate, 8 parts by mass of sodium sulfite, and 2 parts by mass of fluorescent dye, and stirred for 10 minutes. To this were added 120 parts by mass of sodium carbonate and 150

C. was flowed through the jacket at 10 L/min. To this was added 21.27 parts by mass of the prepared surfactant composition for two minutes, and stirred for additional 5 minutes to support the surfactant composition on the particles, and thereby primal detergent particles were prepared.

Then, to this was added 0.916 parts by mass of fatty acid, which was heated to 80° C., by spraying, and stirred for additional 5 minutes. Through this operation, fatty acid reacted with sodium carbonate to give 1 part by mass of soap. To this were added 1.67 parts by mass (effective amount: 1.00 parts by mass) of polyethylene glycol (effective content: 60% by mass), and 1 part by mass of layer clay mineral (Laundrosil DGA powder, Süd-Chemie AG) and 2 parts by mass of crystalline sodium silicate, and stirred for 5 minutes. To this was added 5 parts by mass of zeolite, and stirred for 30 seconds with the main shaft (rotation number: 120 rpm, circumferential velocity: 3.1 m/s) and a chopper (rotation number: 3600 rpm, circumferential velocity: 28 m/s). Mixing conditions of the Loedige mixer was returned to only the main shaft (for an agitating blade, rotation number: 60 rpm, circumferential velocity: 1.6 m/s), and additional 10 parts by mass of zeolite was charged. The mixture was again stirred for 30 seconds under mixing conditions of the main shaft (rotation number: 120 rpm, circumferential velocity: 3.1 m/s) and the chopper (rotation number: 3600 rpm, circumferential velocity: 28 m/s), and discharged to give detergent particles 1. The resultant detergent particles 1 had a bulk density of 795 g/L and an average particle diameter of 315 μm.

Comparative Example 1

Detergent particles 2 were similarly prepared as in Example 3, except that a surfactant composition 2 was prepared as follows and used instead of the surfactant composition used in Example 3. The resultant detergent particles 2 had a bulk density of 795 g/L and an average particle diameter of 315 μm. There was no difference in bulk density or average particle diameter, compared with the detergent particles 1 of Example 3 to which the component a1-1 of the novel ether compound of the present invention was added. The detergent particles having the same bulk density and the same average particle diameter as that of the detergent particles 1 were prepared.

(Preparation of a Surfactant Composition 2)

400 parts by mass of polyoxyethylene alkyl ether and 69 parts by mass of polyethylene glycol (solid content: 60% by mass) were heated to 80° C. To this were added 440 parts by mass of component a2-1 used in Example 2, 960 parts by mass of dodecylbenzensulfonic acid, and 258 parts by mass of aqueous solution of 48% sodium hydroxide, and stirred to give a surfactant composition.

<Washing Test>

Detergent particles 1 and 2 prepared in Example 3 and Comparative Example 1 were subjected to a washing test under the same conditions as that of Example 2. Results are shown in Table 2.

TABLE 2

| | | Example 3 | Comparative example 1 |
| --- | --- | --- | --- |
| | | Detergent particles | |
| | | Detergent particle 1 | Detergent particle 2 |
| Detergency (%) | 20° C. | 87 | 86 |
| | 5° C. | 62 | 37 |

The invention claimed is:

1. A novel ether compound represented by formula (1):

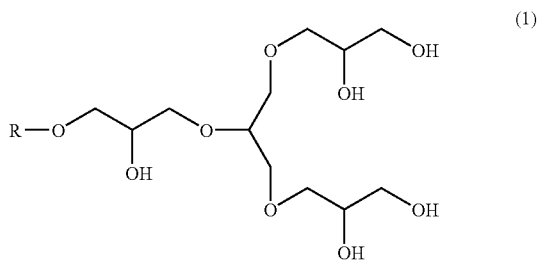

wherein R represents a hydrocarbon group having 4 to 22 carbon atoms.

2. The novel ether compound according to claim 1, wherein R in formula (1) represents an alkyl group having 12 to 18 carbon atoms.

3. A method for producing the novel ether compound according to claim 1 or 2, comprising reacting a compound represented by formula (2) with an alkyl glycidyl ether:

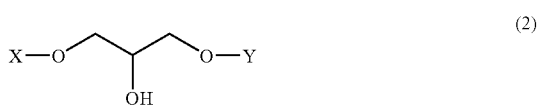

wherein X and Y each represent a group having a protected group.

4. The method for producing the novel ether compound according to claim 3, wherein at least one of X and Y in the compound represented by formula (2) is a group represented by formula (3):

5. A surfactant comprising the novel ether compound according to claim 1 or 2.

6. A detergent composition comprising the novel ether compound according to claim 1 or 2.

7. A polyglyceryl ether composition comprising (a1) the novel ether compound according to claim 1 and (a2) a polyglyceryl monoether having a glycerol condensation degree of 1 to 7 and being other than the ether compound (a1).

8. A detergent composition comprising the polyglyceryl ether composition according to claim 7.

9. The detergent composition according to claim 8, further comprising an alkali agent.

* * * * *